(12) United States Patent
Rockweiler et al.

(10) Patent No.: US 9,604,065 B2
(45) Date of Patent: *Mar. 28, 2017

(54) UNWANTED STIMULATION DETECTION DURING CARDIAC PACING

(71) Applicant: Cardiac Pacemakers, Inc., St. Paul, MN (US)

(72) Inventors: Holly E. Rockweiler, Palo Alto, CA (US); David C. Olson, Eden Prairie, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 39 days.

This patent is subject to a terminal disclaimer.

(21) Appl. No.: 14/469,322

(22) Filed: Aug. 26, 2014

(65) Prior Publication Data
US 2015/0066103 A1 Mar. 5, 2015

Related U.S. Application Data

(60) Provisional application No. 61/872,358, filed on Aug. 30, 2013.

(51) Int. Cl.
*A61N 1/37* (2006.01)
*A61N 1/368* (2006.01)
(Continued)

(52) U.S. Cl.
CPC ......... *A61N 1/3704* (2013.01); *A61B 5/1104* (2013.01); *A61B 5/4848* (2013.01); *A61B 5/726* (2013.01); *A61N 1/3682* (2013.01); *A61N 1/36542* (2013.01); *A61N 1/371* (2013.01); *A61B 5/04001* (2013.01); *A61B 5/1107* (2013.01); *A61B 2562/0219* (2013.01)

(58) Field of Classification Search
CPC ........................................................ A61N 1/37
See application file for complete search history.

(56) References Cited

U.S. PATENT DOCUMENTS 3,903,897 A 9/1975 Woollons et al.
4,114,627 A 9/1978 Lewyn et al.
(Continued)

FOREIGN PATENT DOCUMENTS

WO 2006137067 A2 12/2006

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

The disclosure relates to systems and methods for cardiac rhythm management. In some cases, a system may include a pulse generator for generating pacing pulses for stimulating a heart of a patient; a memory; and a sensor configured to sense a response to a unwanted stimulation and to produce a corresponding sensor signal. A processing circuit may receive the sensor signal for a time after one or more pacing pulses, and may derive a time-frequency representation of the sensor signal based on the received sensor signal. The processing circuit may use the time-frequency representation of the sensor signal to help identify unwanted stimulation. Once unwanted stimulation is detected, the processing circuit may change the pacing pulses to help reduce or eliminate the unwanted stimulation.

11 Claims, 9 Drawing Sheets

(51) Int. Cl.
*A61B 5/00* (2006.01)
*A61N 1/365* (2006.01)
*A61B 5/04* (2006.01)
*A61B 5/11* (2006.01)

(56) References Cited

U.S. PATENT DOCUMENTS

| | | |
|---|---|---|
| 4,892,102 A | 1/1990 | Astrinsky |
| 5,172,694 A | 12/1992 | Flammang et al. |
| 5,222,493 A | 6/1993 | Sholder |
| 5,265,604 A | 11/1993 | Vince |
| 5,324,310 A | 6/1994 | Greeninger et al. |
| 5,331,966 A | 7/1994 | Bennett et al. |
| 5,431,693 A | 7/1995 | Schroeppel |
| 5,443,485 A | 8/1995 | Housworth et al. |
| 5,571,144 A | 11/1996 | Schroeppel |
| 5,601,615 A | 2/1997 | Markowitz et al. |
| 5,649,968 A | 7/1997 | Alt et al. |
| 5,718,720 A | 2/1998 | Prutchi et al. |
| 5,766,225 A | 6/1998 | Kramm |
| 5,843,136 A | 12/1998 | Zhu et al. |
| 5,861,012 A | 1/1999 | Stroebel et al. |
| 5,873,898 A | 2/1999 | Hemming et al. |
| 6,058,328 A | 5/2000 | Levine et al. |
| 6,128,535 A | 10/2000 | Maarse |
| 6,230,061 B1 | 5/2001 | Hartung |
| 6,266,564 B1 | 7/2001 | Hill et al. |
| 6,406,421 B1 | 6/2002 | Grandjean et al. |
| 6,493,586 B1 | 12/2002 | Stahmann et al. |
| 6,522,924 B1 | 2/2003 | Meier |
| 6,772,008 B2 | 8/2004 | Zhu et al. |
| RE38,654 E | 11/2004 | Hill et al. |
| 7,082,331 B1 | 7/2006 | Park et al. |
| 7,245,971 B2 | 7/2007 | Park et al. |
| 7,269,459 B1 | 9/2007 | Koh |
| 7,277,757 B2 | 10/2007 | Casavant et al. |
| 7,299,093 B2 | 11/2007 | Zhu et al. |
| 7,340,302 B1 | 3/2008 | Falkenberg et al. |
| 7,340,306 B2 | 3/2008 | Barrett et al. |
| 7,357,775 B1 | 4/2008 | Koh |
| 7,363,085 B1 | 4/2008 | Benser et al. |
| 7,363,086 B1 | 4/2008 | Koh et al. |
| 7,392,086 B2 | 6/2008 | Sathaye |
| 7,421,296 B1 | 9/2008 | Benser et al. |
| 7,424,321 B2 | 9/2008 | Wariar et al. |
| 7,430,447 B2 | 9/2008 | Min et al. |
| 7,704,211 B1 | 4/2010 | Koh |
| 8,185,202 B2 | 5/2012 | Sathaye |
| 8,260,421 B2 | 9/2012 | Sathaye |
| 8,265,736 B2 | 9/2012 | Sathaye et al. |
| 8,527,051 B1 * | 9/2013 | Hedberg ............ A61N 1/36521 607/11 |
| 2003/0065365 A1 | 4/2003 | Zhu et al. |
| 2006/0241711 A1 | 10/2006 | Sathaye |
| 2007/0118054 A1 | 5/2007 | Pinhas et al. |
| 2008/0021504 A1 | 1/2008 | McCabe et al. |
| 2008/0188904 A1 | 8/2008 | Tehrani et al. |
| 2008/0234556 A1 | 9/2008 | Brooke et al. |
| 2008/0242976 A1 | 10/2008 | Robertson et al. |
| 2009/0024176 A1 | 1/2009 | Yun et al. |
| 2009/0062882 A1 | 3/2009 | Zhang et al. |
| 2009/0099621 A1 | 4/2009 | Lin et al. |
| 2009/0210024 A1 | 8/2009 | Brooke |
| 2010/0125306 A1 | 5/2010 | Mccabe et al. |
| 2010/0256462 A1 | 10/2010 | Rappaport et al. |
| 2010/0305637 A1 | 12/2010 | McCabe et al. |
| 2010/0305638 A1 | 12/2010 | McCabe et al. |
| 2010/0305647 A1 | 12/2010 | McCabe et al. |
| 2011/0004264 A1 | 1/2011 | Siejko et al. |
| 2012/0296387 A1 | 11/2012 | Zhang et al. |

* cited by examiner

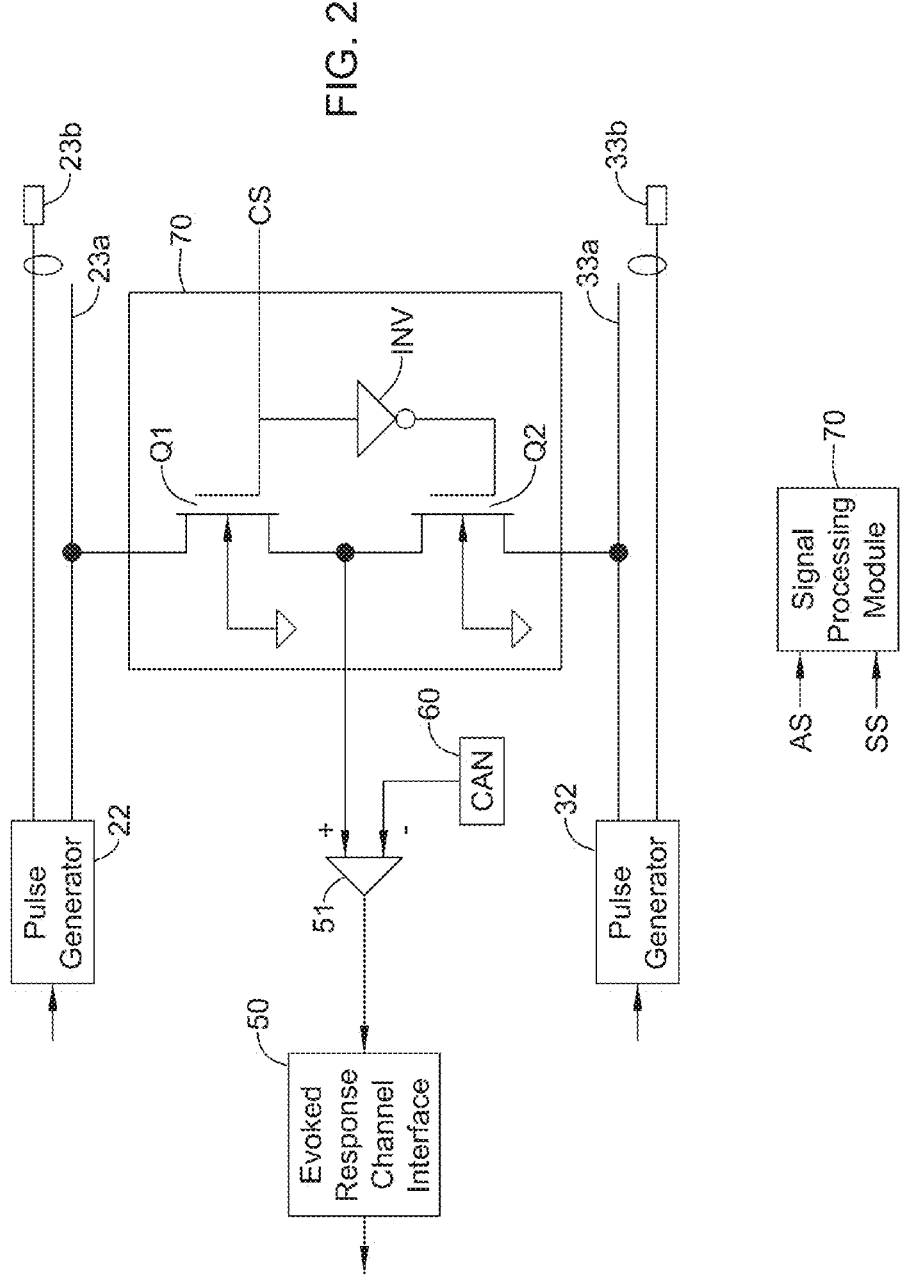

UNWANTED STIMULATION DETECTION DURING CARDIAC PACING

CROSS-REFERENCE TO RELATED APPLICATIONS

This application claims priority under 35 U.S.C. §119 to U.S. Provisional Application Ser. No. 61/872,358, filed Aug. 30, 2013, the entirety of which is incorporated herein by reference.

BACKGROUND

Cardiac rhythm management devices are often implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by, for example, enforcing a minimum heart rate.

Pacemakers are usually implanted subcutaneously or submuscularly on a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes often disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the appropriate chamber via the same or different electrode used for sensing the chamber.

Electrical stimulation of the heart through the internal electrodes can also cause unwanted stimulation of skeletal muscle and/or nerves. The left phrenic nerve, which provides innervation for the diaphragm, arises from the cervical spine and descends to the diaphragm through the mediastinum where the heart is situated. As it passes the heart, the left phrenic nerve courses along the pericardium, superficial to the left atrium and left ventricle. Because of its proximity to the electrodes used for pacing, particularly for left side pacing, the nerve can be stimulated by a pacing pulse. The resulting involuntary contraction of the diaphragm can be quite annoying or painful to the patient, often producing a response that is similar to a hiccup.

SUMMARY

Cardiac rhythm management devices and methods are disclosed for minimizing or eliminating unwanted stimulation of skeletal muscle, such as phrenic nerve stimulation (PS), while treating disorders of cardiac rhythm and similar disorders. In one example, phrenic nerve stimulation is detected during cardiac pacing. If detected, subsequent cardiac pacing pulses are configured to capture the heart and minimize subsequent phrenic nerve stimulation. In this context, "capture" refers to causing sufficient depolarization of the myocardium that a propagating wave of excitation and contraction result (i.e., a heartbeat). It is contemplated that all types of cardiac rhythm management devices may benefit including, but not limited to, bradycardia pacing, anti-tachycardia pacing, and cardiac resynchronization pacing.

In the various embodiments, the determination of whether the phrenic nerve of the patient has been stimulated is based at least in part upon data in the frequency domain. In certain embodiments, the determination of whether the phrenic nerve of the patient has been stimulated by a pacing pulse is based at least in part upon a comparison of data gathered by a sensor over at least one cycle of cardiac activity to a specimen of data which had been previously identified as corresponding to phrenic nerve stimulation; to a specimen of data which had been previously identified as not corresponding to phrenic nerve stimulation; or to a combination of both. In such embodiments, the respective specimens of data, which had been previously identified as corresponding to phrenic nerve stimulation and/or which had been previously identified as not corresponding to phrenic nerve stimulation, may be one or more single instances of the behavior or may include functions of several instances of the behavior. The respective specimens of data may be obtained from the patient or may represent an aggregation of specimens from more than one patient.

In one example, a system for cardiac rhythm management is provided. The system may include a pulse generator for generating pacing pulses for stimulating a heart of a patient, a memory, and a sensor for sensing a response to a stimulation of a phrenic nerve of the patient and to produce a corresponding sensor signal. A processing circuit may be in communication with the memory and the sensor. The processing circuit may be configured to: receive the sensor signal for a time after one or more pacing pulses; derive a time-frequency representation of the sensor signal based on the received sensor signal using wavelets; identify a dominant frequency component in the time-frequency representation of the sensor signal; determine if the dominant frequency component falls within a predetermined frequency range; identify a time of occurrence of the dominant frequency component relative to a pacing pulse; determine if the time of occurrence of the dominant frequency component occurs within a predetermined time window; determine if the phrenic nerve of the patient has been stimulated based, at least in part, on the time-frequency representation of the sensor signal such that the dominant frequency component falls within the predetermined frequency range and the dominant frequency component occurs within the predetermined time window; store a phrenic nerve stimulation event identifier in the memory if the processing circuit determines that the phrenic nerve of the patient has been stimulated; generate pacing pulses for stimulating the heart of a patient that are anticipated to both capture the heart and to minimize phrenic nerve stimulation by the generated pacing pulses; and determine if capture of the heart has been achieved.

In another example, a system for cardiac rhythm management is provided, which may include a pulse generator for generating pacing pulses for stimulating a heart of a patient, a memory, and a sensor configured to sense a response to a stimulation of a phrenic nerve of the patient and to produce a corresponding sensor signal. A processing circuit may be in communication with the memory and the sensor. The processing circuit may be configured to: receive the sensor signal for two or more pacing pulses; perform spectral analysis of the sampled sensor signal, resulting in a spectral analysis output; compare the spectral analysis output to a phrenic nerve stimulation template; determine that the phrenic nerve of the patient has been stimulated if the spectral analysis output is considered to match the phrenic nerve stimulation template; and store a phrenic nerve stimulation event identifier in the memory if the processing circuit determines that the phrenic nerve of the patient has been stimulated. In some cases, the processing circuit may also generate pacing pulses for stimulating the heart of a patient that are anticipated to both capture the heart and to minimize phrenic nerve stimulation.

In yet another example, a method is disclosed for determining if the phrenic nerve of a patient has been stimulated by one or more pacing pulses. The method may include receiving a sensor signal for a time after one or more pacing pulses, wherein the sensor signal is provided by a sensor that can sense a stimulation of the phrenic nerve of the patient. The method may further include determining a time-frequency representation of the sensor signal based on the received sensor signal; identifying a dominant frequency component in the time-frequency representation of sensor signal; determining if the dominant frequency component falls within a predetermined frequency range; identifying a time of occurrence of the dominant frequency component relative to a corresponding pacing pulse; determining if the time of occurrence of the dominant frequency component occurs within a predetermined time window; and determining if the phrenic nerve of the patient has been stimulated based, at least in part, on the time-frequency representation of the sensor signal such that the dominant frequency component falls within the predetermined frequency range and the dominant frequency component occurs within the predetermined time window. These are just some examples.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF DRAWINGS

FIG. 2 is a schematic diagram of an illustrative switching circuit;

FIG. 3 is a block diagram of an illustrative signal processing module;

DESCRIPTION

Figure 1:
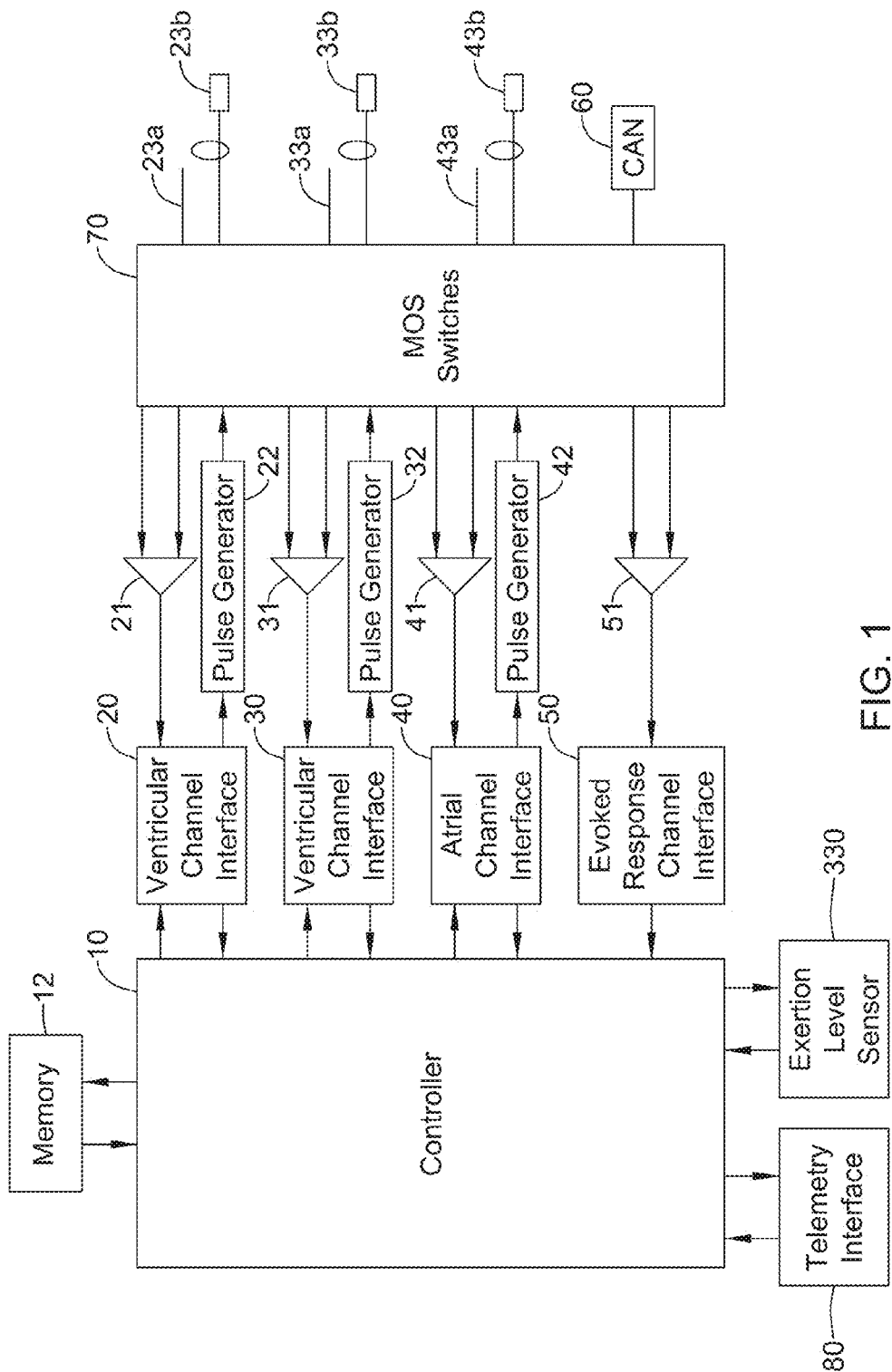
FIG. 1 is a schematic block diagram of an illustrative cardiac rhythm management device.

The following description should be read with reference to the drawings wherein like reference numerals indicate like elements throughout the several views. The drawings, which are not necessarily to scale, are not intended to limit the scope of the disclosure. The description and drawings illustrate several examples.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", "an example", "another example", etc., indicate that the embodiment or example described may include a particular feature, structure, or characteristic, but every embodiment or example may not necessarily include the particular feature, structure, or characteristic. Moreover, such phrases are not necessarily referring to the same embodiment or example. Further, when a particular feature, structure, or characteristic is described in connection with an embodiment or example, it is contemplated that such feature, structure, or characteristic can be used in connection with other embodiments and other examples, whether or not explicitly described unless clearly stated to the contrary.

A schematic block diagram of a multi-site pacemaker having an atrial and two ventricular pacing channels is shown in FIG. 1. It will be appreciated that the device described in FIG. 1 is described for the purpose of providing context for the subsequent discussion, and should not be view as limiting the scope of the disclosure to that particular device. In FIG. 1, the pacemaker may include a control unit that includes a controller 10 communicating with a memory 12 via a bidirectional data bus, where the memory 12 typically includes a ROM (read-only memory) for program storage and a RAM (random-access memory) for data storage. The control unit of the pacemaker also could be implemented by other types of processing circuitry, such as discrete components, a programmable logic array, a microcontroller, a state machine, and/or any other suitable processing circuitry as desired.

In some instances, the control unit of the pacemaker may be capable of operating the pacemaker in a number of programmed modes where a programmed mode defines how pacing pulses are output in response to sensed events and/or expiration of time intervals. Bradycardia pacing modes refer to pacing algorithms used to pace the atria and/or ventricles when the intrinsic atrial and/or ventricular rate is inadequate due to, for example, AV conduction blocks or sinus node dysfunction. Such modes may include either single-chamber pacing, where either an atrium or a ventricle is paced, or dual-chamber pacing in which both an atrium and a ventricle are paced. Another type of pacing is anti-tachycardia pacing where the heart is paced competitively in order to slow an abnormally fast rhythm. Pacemakers can also be employed to improve the coordination of cardiac contractions by timed pacing of selected chambers or sites (e.g. left and right ventricles), termed cardiac resynchronization therapy (CRT).

Additional sensing of physiological data may help the pacemaker change the rate at which it paces the heart in accordance with some parameter correlated to metabolic demand, often referred to as rate-adaptive pacing. One such parameter is the activity level of the patient. In the device of FIG. 1, an exertion level sensor 330, which may include, for example, one or more of an accelerometer, minute ventilation sensor, electrical signal sensor, pressure sensor, an acoustic sensor, and the like, may sense changes in the patient's physical activity. These or other sensors, which are provided on or in the patient, may be configured to provide a sensor signal that is indicative of a response to a stimulation of the phrenic nerve of the patient. In some instances, the sensor signal provided by the exertion level sensor 330 or other sensor may be filtered by the sensor 330 or may be filtered once received by the controller 10. A telemetry interface 80 is often provided for facilitating communication with an external programmer.

For the purpose of brevity in providing an illustrative example, the discussion herein will focus on an accelerometer as a representative sensor. However, it is contemplated that any suitable sensor may be used, including sensors that are suitable for sensing muscle or nerve stimulation such as phrenic nerve stimulation. When the sensor is an accelerometer, it may be a single-axis accelerometer, a two-axis accelerometer, or a three-axis accelerometer, wherein the accelerometers may be discrete or may be integrated. Multi-axis accelerometers will typically be configured such that the axes of the various accelerometers are not aligned and may be configured such that the axes of the accelerometers are substantially mutually orthogonal. Such multi-axis accelerometers may be used to further distinguish movements along the height axis of the recipient, which may correspond to diaphragm motions, from movements at right angles to the height axis, which more typically may correspond to heart movements or incidental movements such may result from an object bumping the chest. When multi-axis accelerometer signals are present, the individual signals may each be processed as described herein and the results of the analysis combined thereafter or the signals from the several accelerometers may be combined to derive an acceleration vector the direction of which is factored into the analysis to be described herein. This should not be taken as disparaging other sensor types.

In order for a pacemaker to control the heart rate in the manner described above, the pacing pulses delivered by the device must achieve "capture," which refers to causing sufficient depolarization of the myocardium that a propagating wave of excitation and contraction result (i.e., a heartbeat). A pacing pulse that does not capture the heart is thus an ineffective pulse. This not only wastes energy from the limited energy resources (battery) of the pacemaker, but can have deleterious physiological effects as well, since a pacemaker that is not achieving capture is not performing its function in enforcing a minimum heart rate. A number of factors can determine whether a given pacing pulse will achieve capture including, for example, the energy of the pulse, which is a function of the pulse's amplitude and duration or width, and the integrity and physical disposition of the pacing lead.

A pacing pulse must exceed a minimum energy value, or capture threshold, to produce a corresponding contraction of the heart. It is desirable for a pacing pulse to have sufficient energy to stimulate capture of the heart without expending energy significantly in excess of the capture threshold. Thus, accurate determination of the capture threshold may provide efficient pace energy management. If the pacing pulse energy is too low, the pacing pulses may not reliably produce a contractile response in the heart and may result in ineffective pacing. If the pacing pulse energy is too high, the patient may experience discomfort due to unwanted extracardiac stimulation and/or the battery life of the device will be shortened.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting an evoked P-wave and/or evoked R-wave, the pacemaker may be able to detect whether the pacing pulse (A-pulse and/or V-pulse) was effective in capturing the heart, that is, in causing a contraction in the respective heart chamber.

In order for a pacemaker to detect whether an evoked P-wave and/or an evoked R-wave occurs immediately following an A-pulse or a V-pulse, a period of time, referred to as the atrial capture detection window or the ventricular capture detection window, respectively, starts after the generation of the corresponding pacing pulse. Sensing channels are normally rendered refractory (i.e., insensitive) for a specified time period immediately following a pacing pulse in order to prevent the pacemaker from mistaking a pacing pulse or after potential for an intrinsic beat. This is done by the pacemaker controller ignoring sensed events during the refractory intervals, which are often defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channels are used for both sensing intrinsic activity and evoked responses, the capture detection window is often defined as a period that supersedes the normal refractory period so that the sensing circuitry within the pacemaker becomes sensitive to an evoked P-wave and/or R-wave.

Capture verification can be performed by delivering a pacing pulse and attempting to sense an evoked response using either the same or different electrodes used for pacing. In the illustrative device shown in FIG. 1, a capture verification test is performed using a dedicated evoked response sensing channel that includes a sense amplifier 51 for sensing an evoked response generated after a pacing pulse is delivered. The amplifier input of the evoked response sensing channel is switched via a switching circuit 70 to selected electrodes of the sensing/pacing channels before the capture verification test is performed. After switching the input of the evoked response sensing channel to the selected electrodes, a pacing pulse is output and an evoked response is either detected within the capture detection window or not, signifying the presence or loss of capture, respectively.

Although the same electrodes can be used for pacing and evoked response detection during a capture verification test, the input of the evoked response sensing channel may be switched to electrodes of another sensing/pacing channel. The particular electrodes used for evoked response detection can be selected in accordance with which electrodes produce a sensing vector that most easily senses an evoked response due to the pacing electrodes. The sense amplifier 51 of the evoked response sensing channel is then blanked during the capture verification test for a specified blanking period following a pacing pulse output by the tested sensing/pacing channel. The blanking period is followed by a capture detection window during which an evoked response may be sensed by the evoked response sensing channel. In some cases, the blanking period may be approximately 10 ms, and the width of the capture detection window may range from 50 to 350 ms, but these are just examples.

The illustrative pacemaker may have an atrial sensing/pacing channel that includes ring electrode 43a, tip electrode 43b, sense amplifier 41, pulse generator 42, and an atrial channel interface 40 which communicates bidirectionally with a port of controller 10. The illustrative pacemaker of FIG. 1 may also include two ventricular sensing/pacing channels that include ring electrodes 23a and 33a, tip electrodes 23b and 33b, sense amplifiers 21 and 31, pulse generators 22 and 32, and ventricular channel interfaces 20 and 30. The electrodes are electrically connected to the device by means of a lead. The ring and tip electrode associated with each channel can be used for bipolar sensing or pacing or, as described below, different electrodes can be connected to each channel through a switching circuit 70 to result in different unipolar sensing or pacing vectors. The sensing circuitry of the pacemaker may generate atrial and ventricular sense signals when voltages sensed by the electrodes exceed a specified threshold.

The illustrative pacemaker may also include an evoked response sensing channel that includes an evoked response channel interface 50 and a sense amplifier 51. The channel interfaces may include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude, if desired.

The controller 10 of the pacemaker may control the overall operation of the device in accordance with programmed instructions stored in memory 12. The controller 10 interprets sense signals from the sensing channels and controls the delivery of pacing pulses in accordance with a pacing mode. The controller 10 may interface with a switching circuit 70 through which the electrodes are connected to the sense amplifiers and pulse generators. The controller 10 may be configured to connect the amplifiers and/or pulse generators to selected tip or ring electrodes of any of the sensing/pacing channels that connect through the switching circuit 70. Each sense amplifier may amplify the voltage difference between two inputs, and the inputs may be selected from any of the tip or ring electrodes or the pacemaker case or can 60, which may also be electrically connected to the switching circuit. The controller 10 may have the capability of connecting a pulse generator such that a pacing voltage pulse appears across any of the tip or ring electrodes or across an electrode and the can 60. A particular set of electrodes and one or more pulse generators used to output pacing pulses may be referred to herein as a pacing configuration.

The switching circuit 70 may be implemented as an array of MOSFET transistors controlled by outputs of the controller 10. FIG. 2 shows a schematic diagram of a portion of a switching circuit. In the illustrative switch circuit, a pair of MOSFET transistors Q1 and Q2 along with an inverter INV form a double-pole switch that switches one of the inputs to sense amplifier 51 between ring electrodes 23a and 33a in accordance with a control signal CS from the controller 10. The other input is shown as being connected to can 60, but in some instances, it may also be switched to one of the electrodes by the switching circuit. In a more complicated version of the same basic pattern, the switching circuit 70 may be able to switch the amplifier inputs or pulse generator outputs to any of the tip or ring electrodes of the sensing/pacing channels or to the can 60, as desired.

FIG. 3 is a block diagram of an illustrative signal processing module 300. In some instances, the illustrative signal processing module 300 may be configured to perform a comparison between an accelerometer signal and a stored template for cardiac activity. The illustrative signal processing module 300 may be incorporated into the controller 10 either as code executed by the microprocessor or as one or more discrete hardware components, and may compare an accelerometer signal obtained during a pacing time window with a stored template for cardiac activity. The comparison may be performed in either the time domain or the frequency domain, or both.

Pacing pulses produced by cardiac rhythm management devices can incidentally stimulate the phrenic nerve and cause contraction of the diaphragm of the patient. It is also possible for unipolar pacing configurations to produce a pacing vector that stimulates the pectoral muscles overlying the internal electrodes of the can, resulting in so-called pocket twitch. Both skeletal muscle stimulation and nerve stimulation can be annoying or painful to a patient. Abrupt contractions of either the pectoral muscles or the diaphragm can impart an acceleration to the implanted housing of the pacemaker, and typically results in a sensor signal that can be correlated to the unwanted stimulation.

To detect whether pacing pulses are producing such unwanted stimulation, the controller 10 may be configured to use the accelerometer 330 (or other sensor) to sense any accelerations experienced by the device housing (e.g. can) that coincide with the output of a pacing pulse. Contraction of the heart and the resulting heart sounds can impart an acceleration to the device housing (e.g. can) that coincides with a pacing pulse. In order to distinguish desired stimulation (e.g. heart capture) from unwanted stimulation (e.g. skeletal muscle contraction), signal processing techniques can be applied to the sensor signal.

Figure 4A:
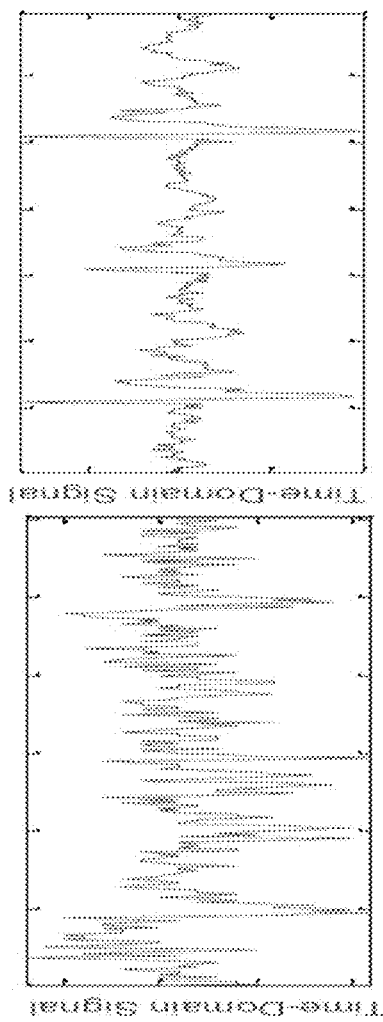
FIG. 4A shows an illustrative time domain signal that is meant to be representative of a sensor output signal provided by an accelerometer that is located in or on a patient, in the absence of phrenic nerve stimulation.
Figure 4B:
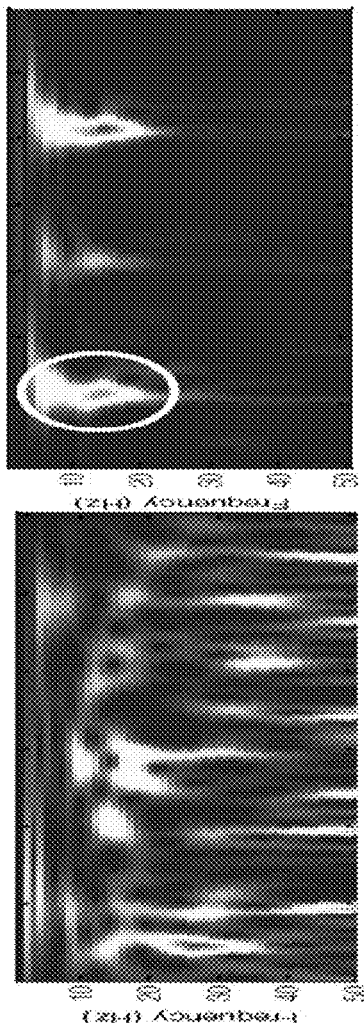
FIG. 4B illustrates the result of a wavelet analysis of the time domain signal of FIG. 4A.
Figure 4C:
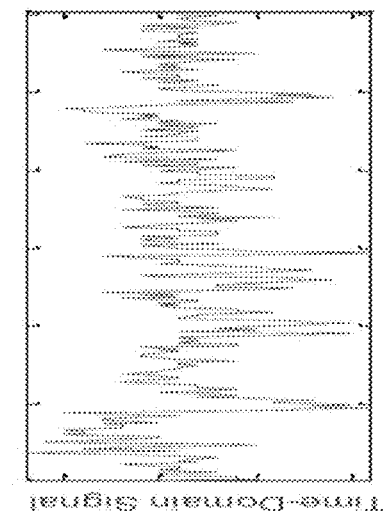
FIG. 4C shows an illustrative time domain signal that is meant to be representative of a sensor output signal provided by an accelerometer that is located in or on a patient, in the presence of phrenic nerve stimulation.
Figure 4D:
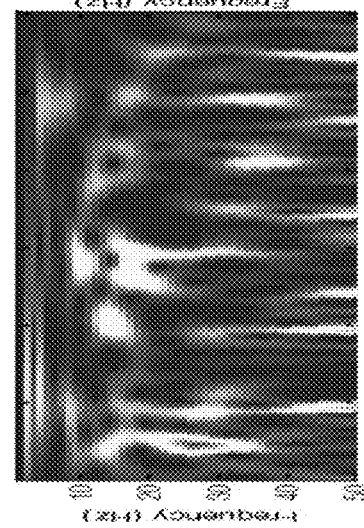
FIG. 4D illustrates the result of a wavelet analysis of the time domain signal of FIG. 4C.

In some instances, signal processing may make use of a wavelet transformation of an exertion level sensor signal such as an accelerometer signal. The accelerometer signal may be converted into a set of wavelets, the set of wavelets including continuous wavelets, wavelets at a fine scale, and/or wavelets of a coarse scale. Wavelet analysis may be viewed as presenting the signal in a plot of the frequency components of the signal versus time with a representation of the signal intensity by frequency in that domain. See FIGS. 4A-4D in which FIGS. 4A and 4C illustrate time domain signals from an exertion related signal (e.g. accelerometer) which includes no phrenic nerve stimulation and an exertion related signal which does include phrenic nerve stimulation (PS), respectively. FIGS. 4B and 4D show an illustrative wavelet analyses (using Morlet wavelet processing) corresponding to the exertion related signals of FIGS. 4A and 4C, respectively.

Wavelet analysis may, for example, allow the signal to be characterized as, for example, including large amplitude shallow deflections, large amplitude steep deflections, small amplitude shallow deflections, or small amplitude steep deflections, and to determine whether the deflections occur at a consistent time and frequency relative to the pacing signal, thereby being suitable for distinguishing phrenic nerve stimulation related signals from other exertion related signals. In some instances, the wavelet analysis may be derived using Morlet wavelets. In yet other embodiments, the wavelet analysis may be derived using continuous wavelets, and/or any other suitable wavelet signal processing technique.

Within a plot of the frequency components of the signal versus time with a representation of the signal intensity by frequency in that domain resulting from wavelet analysis such as that of FIGS. 4A and 4C, the frequency and time components of a signal may be determined by viewing the plot as a contour map of the signal intensity. In some cases, a contour that surrounds the region of maximum signal intensity may be selected and a centroid or center of mass of that contour may be computed. One familiar with the wavelet plots in question will readily determine a signal intensity threshold appropriately elevated above the background signal intensity to serve to select an intensity level contour for the computation of the centroid. The frequency and time corresponding to the centroid may then be taken to represent the dominant frequency and the corresponding time of the event. This is one illustrative method of identifying a dominate frequency and the corresponding time of an event.

Figure 5:
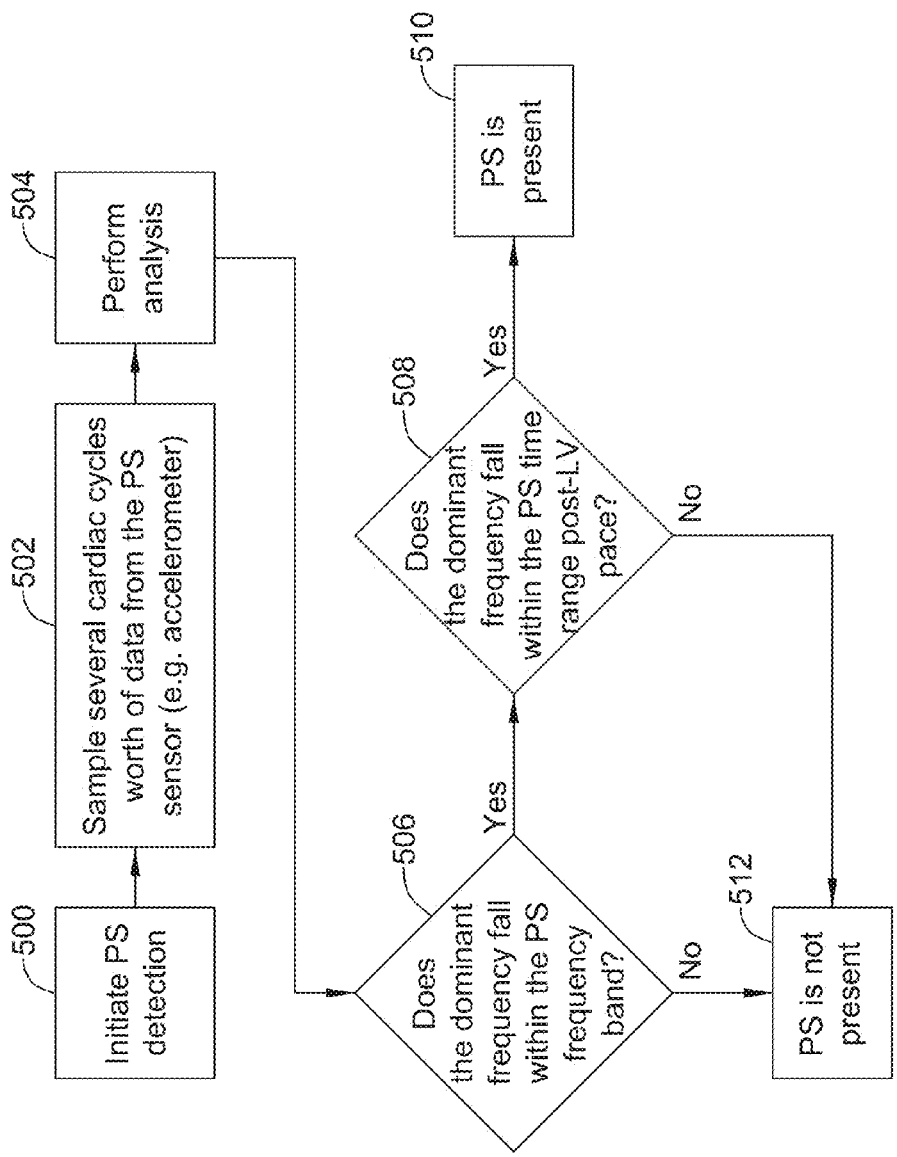
FIG. 5 is a flow diagram shown an illustrative method of determining if phrenic nerve stimulation is present or absent.

An illustrative detection and analysis of exertion related signals is illustrated somewhat schematically in the flow diagram of FIG. 5. In the illustrative method, phrenic nerve stimulation detection is initiated (500) to sample the exertion related signal (502) for the duration of several cardiac cycles of left ventricular cardiac activity (50-350 ms) which is stored and analyzed (504) to extract a dominant frequency. The dominant frequency is then checked (506) to determine if the dominant frequency falls within the phrenic nerve stimulation frequency band. If the dominant frequency does not fall within the phrenic nerve stimulation frequency band, phrenic nerve stimulation is determined to be not present (512). If the dominant frequency does fall within the phrenic nerve stimulation frequency band, then the dominant frequency may be further checked (508) to determine if the dominant frequency occurs within an appropriate time window relative to left ventricular stimulation pacing pulses. If this condition is also met, then phrenic nerve stimulation is determined to be present (510), and if not, phrenic nerve stimulation is determined not to be present (512). In some instances, the dominant frequency component is determined as a mean, or other central tendency measure, of two or more dominant frequency components identified for two or more pacing pulses.

Figure 6:
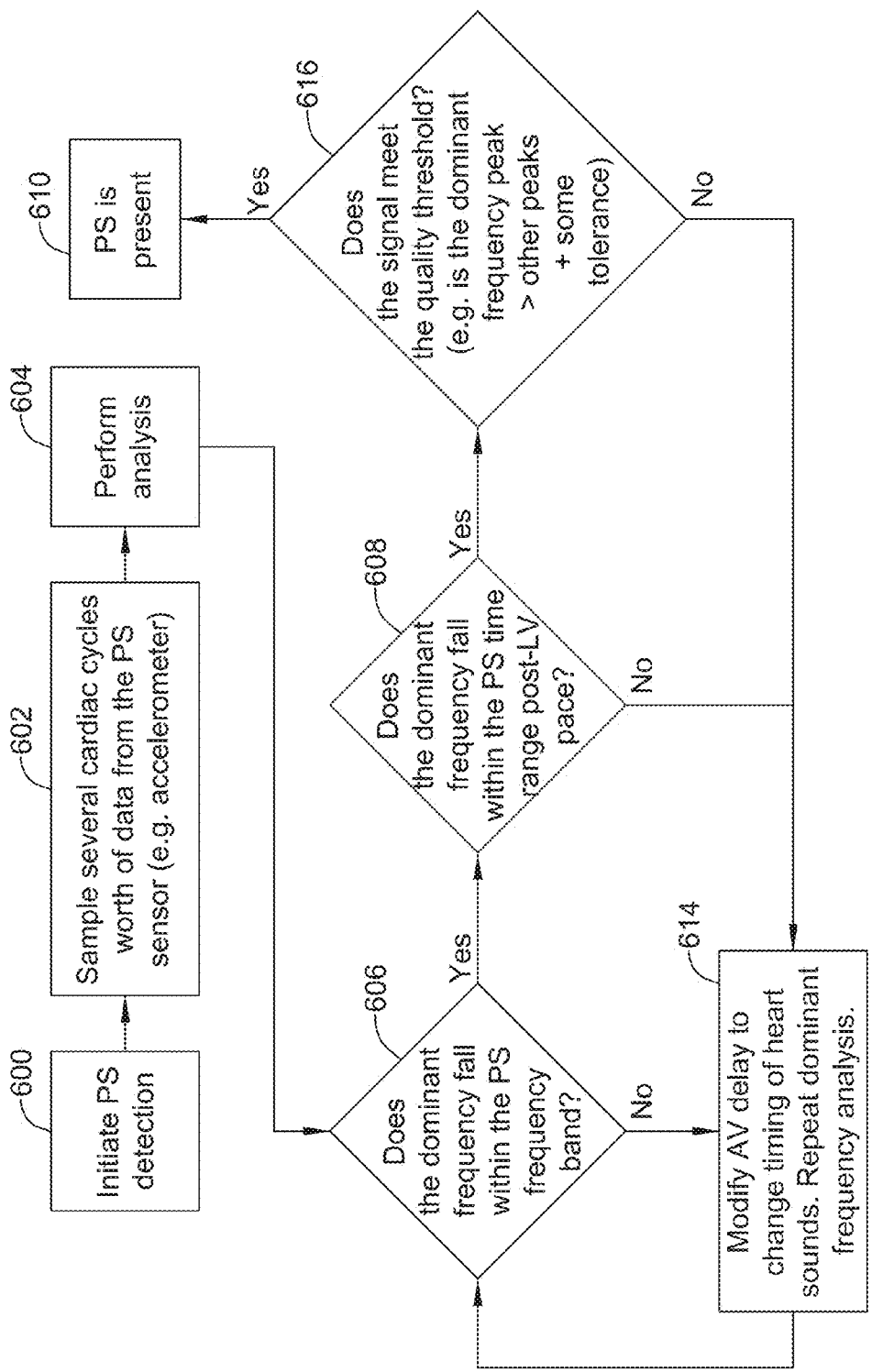
FIG. 6 is a flow diagram shown another illustrative method of determining if phrenic nerve stimulation is present or absent.

Another illustrative detection and analysis scheme, which adds confirmation of the detection of phrenic nerve stimulation, is illustrated schematically in the flow chart of FIG. 6, in which phrenic nerve stimulation detection is initiated (600), sampled (602), and analyzed (604) to extract a dominant frequency. The dominant frequency may be checked (606) to determine if the dominant frequency falls within a phrenic nerve stimulation frequency band as in the method of FIG. 5. Should the dominant frequency not fall within the phrenic nerve stimulation frequency band, the analysis may continue by modifying (614) the atrio-ventricular timing to change the timing of heart sounds and repeating the dominant frequency analysis. As before, when the dominant frequency does fall within the phrenic nerve stimulation frequency band, the dominant frequency may be further checked (608) to determine if the dominant frequency occurs within an appropriate time window relative to left ventricular stimulation pacing pulses. If this fails to be true, the analysis may continue by modifying (614) the atrio-ventricular timing to change the timing of heart sounds, and the dominant frequency analysis may be repeated.

If the dominant frequency does fall within the phrenic nerve stimulation frequency band and the dominant frequency occurs within an appropriate time window relative to left ventricular stimulation pacing pulses, the signal may be further checked (616) to see if the signal meets other predetermined signal quality criteria such as, for example, the magnitude of the dominant frequency peak being greater than the magnitude of other peaks in the data by a specified tolerance and/or a peak sharpness requirement is met whereupon the phrenic nerve stimulation is deemed to be present (610). Should the signal fail to meet the predetermined quality criteria, the atrio-ventricular timing may again be changed (614), and the dominant frequency analysis cycle may be repeated.

In some instances, the processing circuit may determine that the phrenic nerve of the patient has been stimulated if a dominant frequency from a wavelet analysis is seen to occur at a substantially consistent time after each of two or more pacing pulses and at substantially consistent frequencies (e.g. frequencies consistent with phrenic nerve stimulation).

Figure 7:
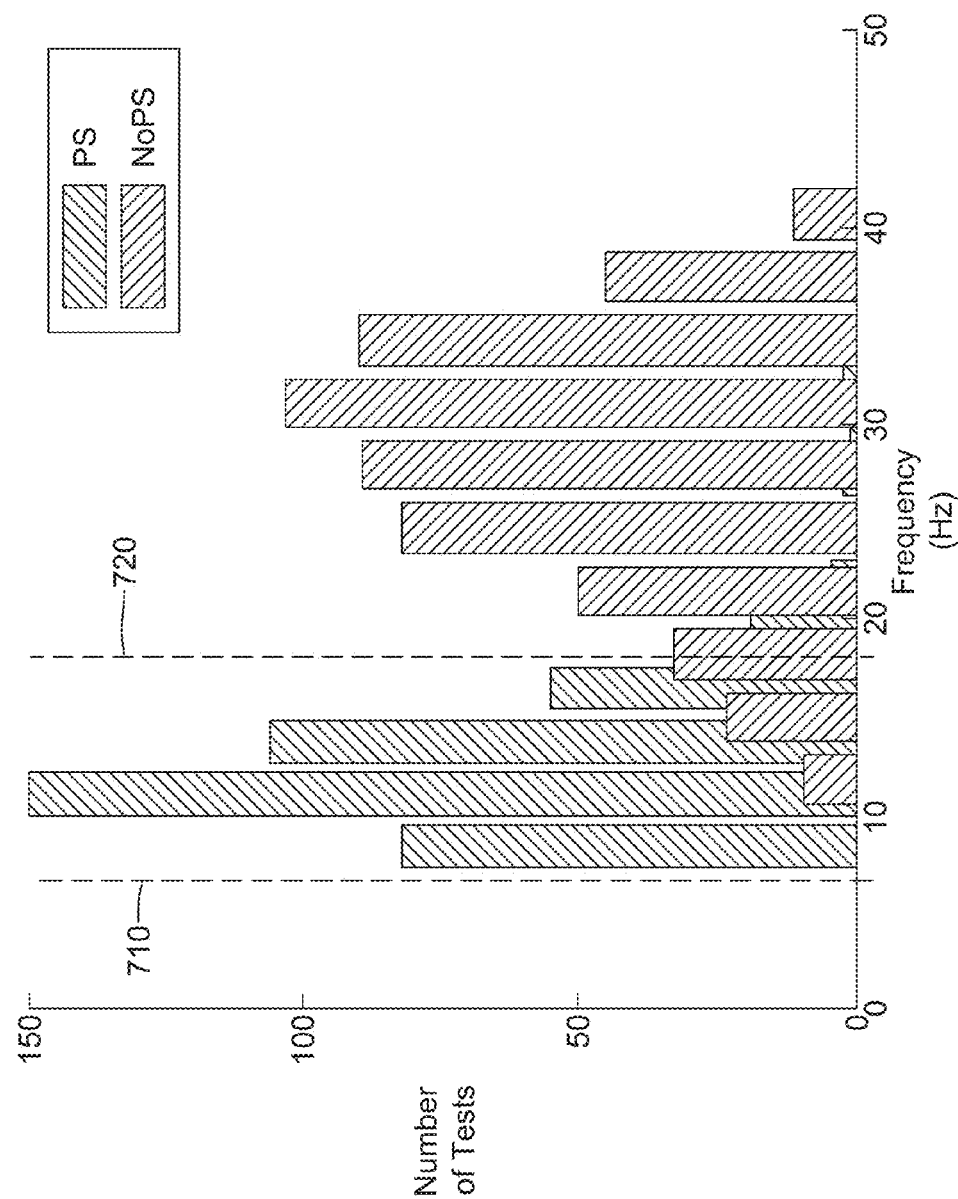
FIG. 7 illustrates a combined histogram of observed frequency centroids for wavelets in which phrenic nerve stimulation is present and in which phrenic nerve stimulation is absent.
Figure 8:
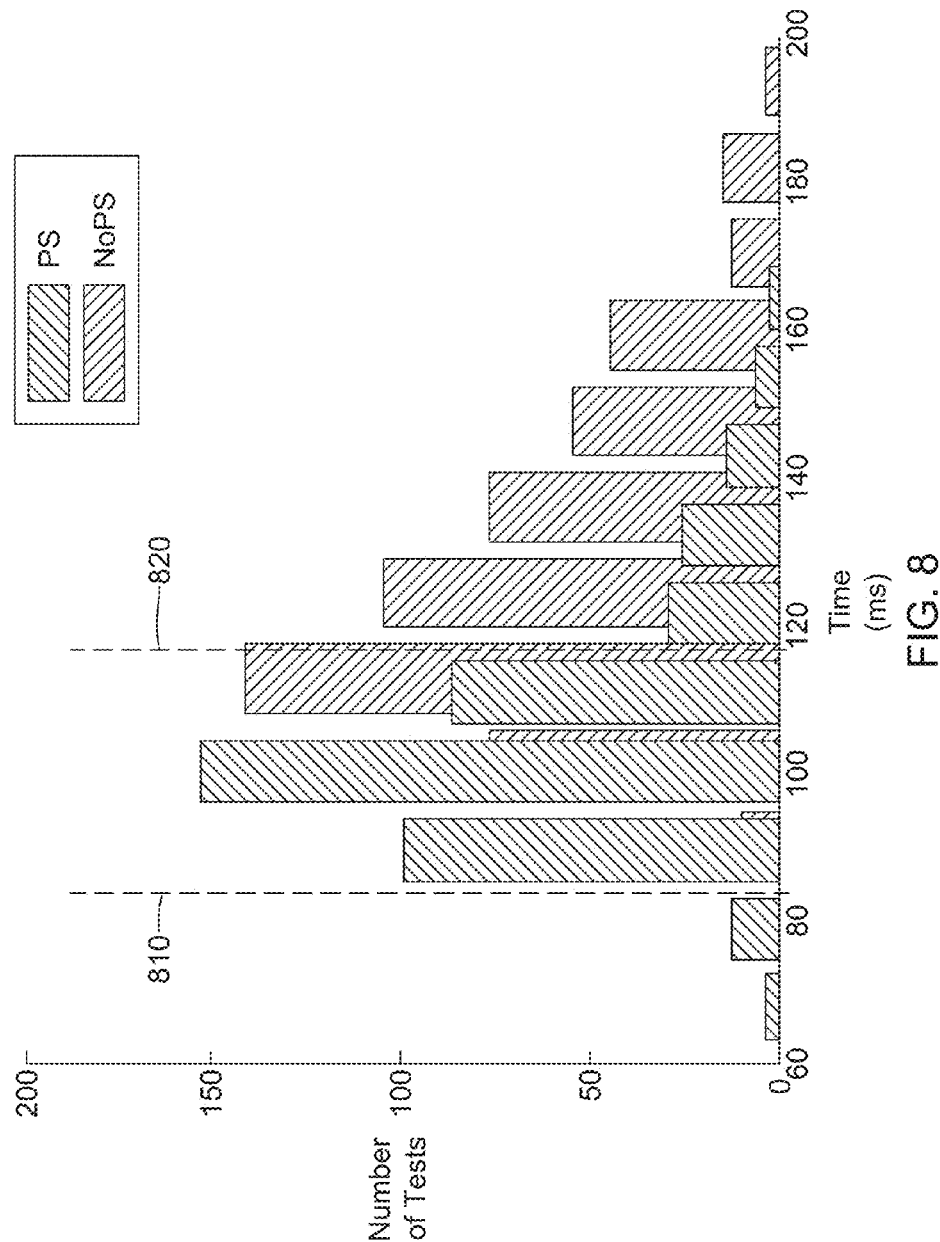
FIG. 8 illustrates a combined histogram of observed time interval centroids for wavelets in which phrenic nerve stimulation is present and in which phrenic nerve stimulation is absent.

For the purpose of determining a predetermined phrenic nerve stimulation frequency band and a predetermined appropriate time window relative to left ventricular stimulation pacing pulses, information related to a number phrenic nerve stimulation tests may be collected from the patient prior to programming, or from a number of other patients, and may then be analyzed by, for example, plotting the data as a frequency histogram (see FIG. 7) and/or as a time delay histogram (see FIG. 8). In both instances, the frequency and time associated with phrenic nerve stimulation or the lack thereof may be determined from, for example, the centroid of a region within the wavelet plot as discussed above. In the respective figures, accelerometer data from 20 patients was collected and analyzed together. As can be seen in FIG. 7, the majority of phrenic nerve stimulations occurred in a frequency band between a lower bound (710) at about 7 Hz and an upper bound (720) at about 18 Hz. Similarly, in FIG. 8 it will be seen that the majority of phrenic nerve stimulations occurred within a time window between a lower bound (810) of about 90 ms and an upper bound (820) of about 110 ms following a left ventricle pacing pulse.

Figure 9:
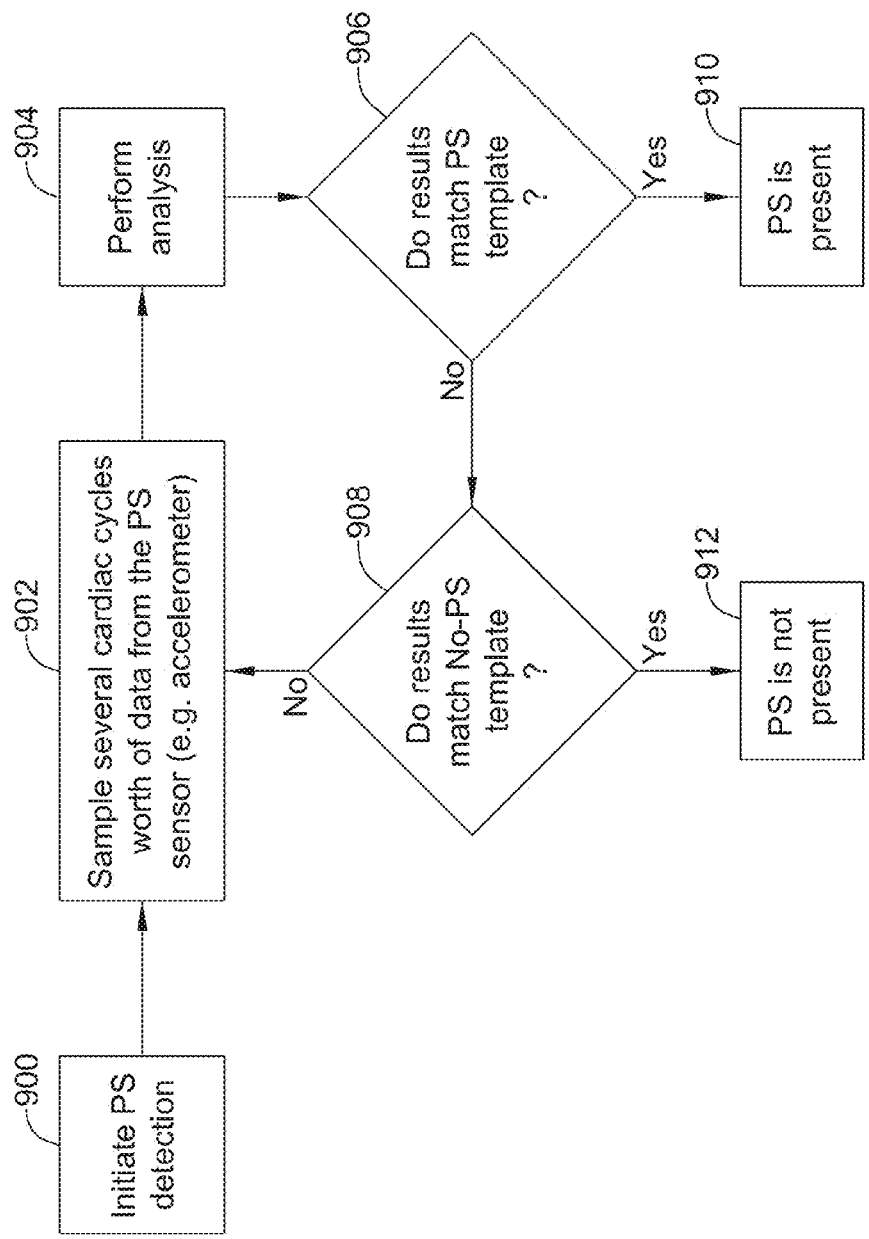
FIG. 9 is a flow diagram showing another illustrative method of determining if phrenic nerve stimulation is present or absent in a patient.

FIG. 9 is a flow diagram illustrating an another illustrative method of determining if phrenic nerve stimulation is present or absent in a patient. Following initiation (900) of phrenic nerve stimulation detection, several cardiac cycles of data from a sensor such as an accelerometer, minute ventilation sensor, electrical signal sensor, pressure sensor, an acoustic sensor, and the like may be sampled (902) and subjected to spectral analysis (904) by a processing circuit in communication with a memory and the sensor. The output of the spectral analysis may then be compared (906) to a stored template of detected phrenic nerve stimulation. The stored template of a phrenic nerve stimulation event may be a patient specific template or a population based template. In some cases, either template may subsequently be modified and/or updated by the acquisition and incorporation of subsequent phrenic nerve stimulation events.

In this illustrative method, if the spectral analysis output matches the stored template of detected phrenic nerve stimulation, phrenic nerve stimulation is deemed to be present (910). If the spectral analysis output does not match the stored template of detected phrenic nerve stimulation, spectral analysis output may be compared (908) to a stored template of cardiac activity in which phrenic nerve stimulation is absent. If the spectral analysis output matches the stored template of cardiac activity in which phrenic nerve stimulation is absent, phrenic nerve stimulation is deemed not to have occurred (912). If the spectral analysis output does not match the stored template of cardiac activity in which phrenic nerve stimulation is present and does not match the stored template of cardiac activity in which phrenic nerve stimulation is absent, the sampling (902) of several cardiac cycles of sensor data is repeated and the analysis may be repeated.

In this example, the illustrative signal processing module 300 of FIG. 3 may be incorporated into the controller 10, which may be considered a processing circuit, either as code executed by a microprocessor or as one or more discrete hardware components, and may be configured to compare, for example, an accelerometer signal obtained during the pacing time window with one or both of stored templates of cardiac activity in which phrenic nerve stimulation is present and of cardiac activity in which phrenic nerve stimulation is absent. The comparison may be performed in the frequency domain. In some instances, the illustrative signal processing module 300 may be a matched finite impulse response filter that performs a cross-correlation between the accelerometer signal and a previously recorded and stored recorded template. The templates may be represented in that case by the filter coefficients of the matched filter (i.e., the impulse response of the filter corresponds to a time-reversed version of the template of cardiac activity). In some instances, in addition to determining if the comparison of the spectral analysis output to a phrenic nerve stimulation template to determine if phrenic nerve stimulation has occurred, the spectral analysis output may be compared to a non-phrenic nerve stimulation template to determine if phrenic nerve stimulation has not occurred.

In some instances, signal processing may make use of an analysis of the accelerometer or other exertion level sensor signal by examination of a power spectrum of the signals. For example, an illustrative method may include: receiving a sensor signal for a time period after one or more pacing pulses, wherein the sensor signal is provided by a sensor that can sense a stimulation of the phrenic nerve of the patient; derive a power spectrum based on the received sensor signal during the time period after the one or more pacing pulses; and determine if the phrenic nerve of the patient has been stimulated based, at least in part, on the derived power spectrum.

Figure 10:
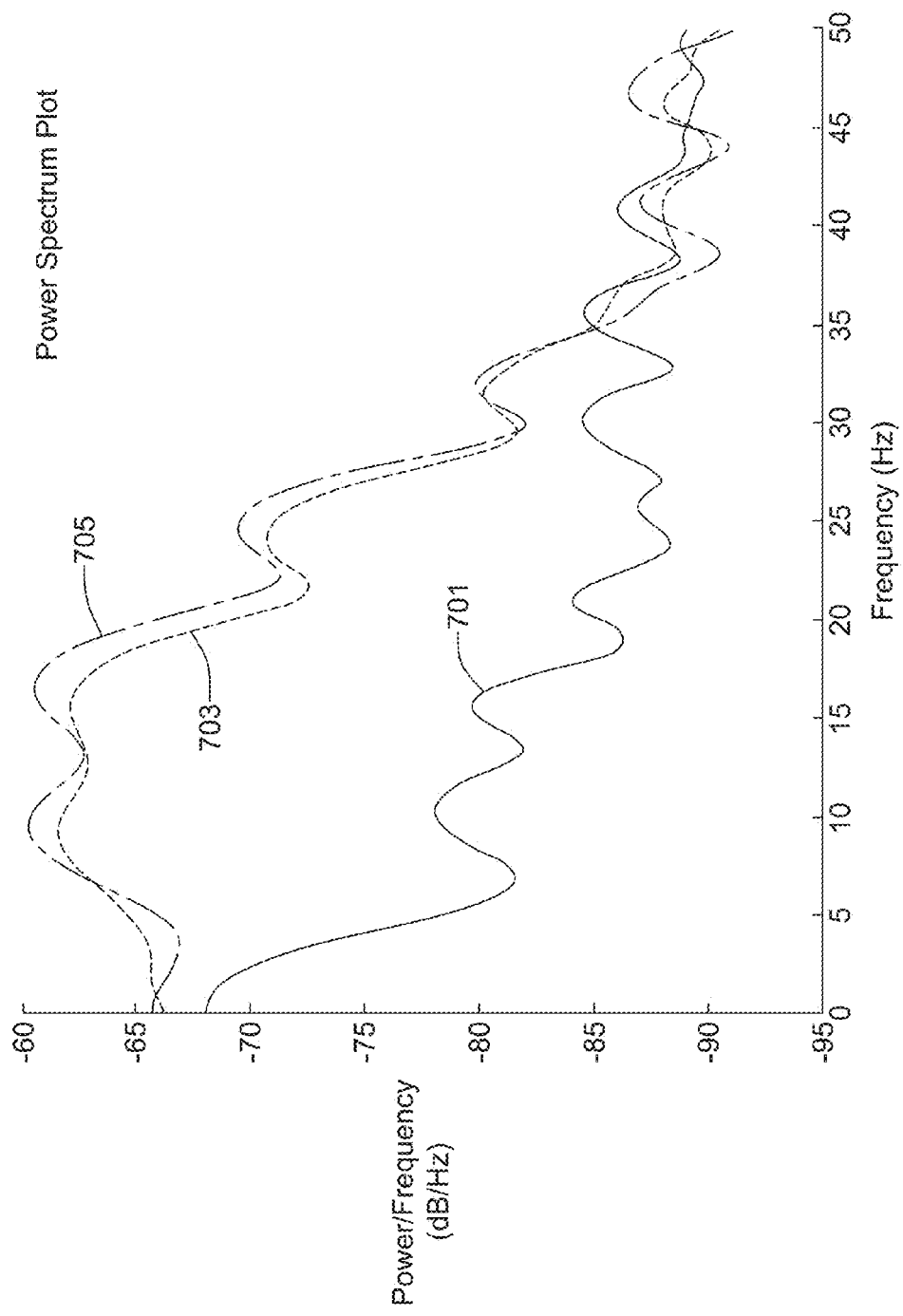
FIG. 10 illustrates exemplary power spectra representative of the presence or absence of phrenic nerve stimulation.

The power spectrum may be considered to be a plot of power divided by frequency (dB/Hz) versus frequency (Hz) as illustrated in FIG. 10. A representative power spectrum of an accelerometer output or other exertion level sensor obtained when no phrenic nerve stimulation is present exhibits lower power at low frequencies as shown by curve 701. This curve 701 represents the power spectrum of an illustrative acceleration sensor signal during a time window following a pacing pulse. In some cases, the power spectrum may be an aggregate power spectrum corresponding to time periods following two or more pacing pulses. As can be seen, when phrenic nerve stimulation is present, the power spectrum of the sensor signal may exhibit greater power at those low frequencies as shown by curve 703, both when the phrenic nerve stimulation occurs relatively soon after the pacing pulse as well as when the phrenic nerve stimulation occurs relatively late (705) after the pacing pulse. When no phrenic nerve stimulation is present, the power spectrum of the sensor signal may exhibit substantially lower power at those same low frequencies, as shown by curve 701. In some cases, the derived power spectrum may be compared to one or more power spectrum templates, such as a power spectrum template that corresponds to phrenic nerve stimulation and/or a power spectrum template that corresponds to no phrenic nerve stimulation.

While these examples are described with respect to phrenic nerve stimulation, it is contemplated that the same approach may be used to detect other unwanted stimulation events. In any event, once it is determined that unwanted stimulation is occurring with pacing pulses, the controller 10 may make adjustments in the operation of the device. In some cases, capture verification tests may be performed as the pacing pulse energy is reduced until a pacing pulse energy is found that achieves both capture and produces no (or reduced) unwanted stimulation. In some instances, the pacing configuration can be varied. For example, different pacing vectors can be used by switching the output of a pulse generator to different electrodes with the switching circuit 70. Switching from a unipolar to a bipolar pacing configuration, for example, may help reduce pacing pulses from causing pectoral muscle contractions or other unwanted stimulation. In some instances, the timing of the pacing pulses may be changed. For example, the AV, VV or other delays may be changed to help alleviate or minimize the unwanted stimulation.

Other pacing configurations with different pacing vectors and/or different time delays may be less likely to stimulate, for example, the phrenic nerve. In the case of multi-site pacing, different pacing configurations using fewer or different pacing sites may also be tried. The configuration of the pacemaker may be varied automatically by the pacemaker during an initial or subsequent programming phase; may be varied manually by an operator during an initial or subsequent programming phase; and/or may be adaptively varied by the pacemaker in response to sensed phrenic nerve stimulation.

In the foregoing Description, various features have been grouped together in a limited number of examples for the purpose of streamlining the disclosure. This method of disclosure is not to be interpreted as reflecting an intention that the examples require more features than are expressly recited in each appended claim. Similarly, the failure of any single example to expressly recite a given subset of the features found distributed among the descriptions of other examples is not to be interpreted as reflecting an intention that the feature subset not be considered disclosed. It is contemplated that features, structures, or characteristics disclosed in one example can be used in other examples, whether or not explicitly described unless clearly stated to the contrary.

Various modifications and alterations will become apparent to those skilled in the art without departing from the scope and principles of this disclosure, and it should be understood that this disclosure is not to be unduly limited to the particular examples set forth hereinabove.

What is claimed is:

1. A system for cardiac rhythm management comprising:
a pulse generator for generating pacing pulses for stimulating a heart of a patient;
a memory;
a sensor configured to sense a response to a stimulation of a phrenic nerve of the patient and to produce a corresponding sensor signal;
a processing circuit in communication with the memory and the sensor, the processing circuit configured to:
receive the sensor signal for a time after one or more pacing pulses;
derive a time-frequency representation of the sensor signal based on the received sensor signal using wavelets;
identify a dominant frequency component in the time-frequency representation of sensor signal;
determine if the dominant frequency component falls within a predetermined frequency range;
identify a time of occurrence of the dominant frequency component relative to a corresponding pacing pulse;
determine if the time of occurrence of the dominant frequency component occurs within a predetermined time window;
determine if the phrenic nerve of the patient has been stimulated based, at least in part, on the time-frequency representation of the sensor signal such that the dominant frequency component falls within the predetermined frequency range and the dominant frequency component occurs within the predetermined time window;
store a phrenic nerve stimulation event identifier in the memory if the processing circuit determines that the phrenic nerve of the patient has been stimulated.

2. The system of claim 1, wherein the sensor includes one or more of an accelerometer, a minute ventilation sensor, an electrical signal sensor, a pressure sensor, and an acoustic sensor that is/are configured to sense a measure indicative of stimulation of the phrenic nerve of the patient.

3. The system of claim 1, wherein the sensor includes an accelerometer that is configured to sense an acceleration indicative of a response to a stimulation of the phrenic nerve of the patient.

4. The system of claim 1, wherein the dominant frequency component is a mean of two or more dominant frequency components resulting from each of two or more pacing pulses.

5. The system of claim 1, wherein the dominant frequency component is determined by a centroid of a feature in a time-frequency representation of the sensor signal based on the received sensor signal using wavelets.

6. The system of claim 1, wherein the time of occurrence of the dominant frequency component relative to the predetermined time window is determined by a centroid of a feature in a time-frequency representation of the sensor signal based on the received sensor signal using wavelets.

7. The system of claim 1, wherein the processing circuit further determines if the dominant frequency component meets a predetermined quality threshold, and wherein the phrenic nerve of the patient is determined to have been stimulated when the dominant frequency component meets a predetermined quality threshold, the dominant frequency component falls within the predetermined frequency range and the dominant frequency component occurs within the predetermined time window.

8. The system of claim 1, wherein the pulse generator provides the pacing pulse to the heart of the patient after an atrio-ventricular delay, and wherein the pulse generator changes the atrio-ventricular delay, and the processing circuit repeats the receiving through determining steps to determine if the phrenic nerve of the patient has been stimulated.

9. The system of claim 1, wherein the time-frequency representation of the sensor signal is derived using Morlet wavelets and/or a continuous wavelet transform.

10. The system of claim 1, wherein the processing circuit further is configured to generate pacing pulses for stimulating the heart of a patient that are anticipated to both capture the heart and to minimize phrenic nerve stimulation by the generated pacing pulses; and
determine if capture of the heart has been achieved.

11. A method for determining if a phrenic nerve of a patient is stimulated by one or more pacing pulses of a cardiac pacemaker, comprising:
receiving a sensor signal for a time after one or more pacing pulses, wherein the sensor signal is provided by a sensor that can sense a stimulation of the phrenic nerve of the patient;
determining a time-frequency representation of the sensor signal based on the received sensor signal;
identifying a dominant frequency component in the time-frequency representation of sensor signal;
determining if the dominant frequency component falls within a predetermined frequency range;
identifying a time of occurrence of the dominant frequency component relative to a corresponding pacing pulse;
determining if the time of occurrence of the dominant frequency component occurs within a predetermined time window; and
determining if the phrenic nerve of the patient has been stimulated based, at least in part, on the time-frequency representation of the sensor signal such that the dominant frequency component falls within the predetermined frequency range and the dominant frequency component occurs within the predetermined time window.

* * * * *